United States Patent
Furusawa

[11] Patent Number: 6,161,035
[45] Date of Patent: Dec. 12, 2000

[54] FLUORESCENCE DIAGNOSTIC APPARATUS

[75] Inventor: Koichi Furusawa, Tokyo, Japan

[73] Assignee: Asahi Kogaku Kogyo Kabushiki Kaisha, Tokyo, Japan

[21] Appl. No.: 09/069,210

[22] Filed: Apr. 29, 1998

[30] Foreign Application Priority Data

Apr. 30, 1997 [JP] Japan .................................. 9-112854

[51] Int. Cl.[7] .................................................. A61B 6/00
[52] U.S. Cl. ...................... 600/476; 600/173; 600/160; 250/461.2
[58] Field of Search ................................ 600/476, 160, 600/172, 173, 174, 178, 182, 477, 109; 356/302, 303; 250/234, 461.2

[56] References Cited

U.S. PATENT DOCUMENTS

| | | | |
|---|---|---|---|
| 5,419,312 | 5/1995 | Arenberg et al. | 128/6 |
| 5,506,912 | 4/1996 | Nagasaki et al. | |
| 5,701,903 | 12/1997 | Sano et al. | |
| 5,772,580 | 6/1998 | Utsui et al. | |
| 5,773,835 | 6/1998 | Sinofsky. | |
| 5,840,017 | 11/1998 | Furusawa et al. | |
| 5,879,284 | 3/1999 | Tsujita | 600/109 |
| 6,019,721 | 2/2000 | Holmes et al. | 600/167 |

*Primary Examiner*—Marvin M. Lateef
*Assistant Examiner*—Shawna J Shaw
*Attorney, Agent, or Firm*—Greenblum & Bernstein, P.L.C.

[57] ABSTRACT

A fluorescence diagnostic apparatus is provided in which a site to be subjected to spectrometry can be designated in an image of a diagnostic living tissue which is taken via an endoscope, and the designated site can be automatically subjected to spectrometry. Fluorescence from the inner wall of a body cavity of a patient is conveyed in an image guide fiber bundle (14) of an endoscope (10), and then emitted as parallel light from an eye lens (16a). A partial reflection mirror in a mirror box (50) allows most of the light to transmit therethrough, and reflects the other portion of the light. From the transmitted light, an image of the inner wall of the body cavity is formed by an imaging lens. The image is taken by a fluorescence-observation CCD (34), and displayed by a display of a video monitor device (60). On the other hand, from the light reflected by the partial reflection mirror, an aerial image of the inner wall of the body cavity is formed by an imaging lens. A touch panel is disposed on the display of the video monitor device (60). When a part of the touch panel is pressed, the tip end of a spectrometry-fiber probe of a spectroscope (39) is moved by an X-Y table (31) to a position in the aerial image which is equivalent to the pressed site of the touch panel.

8 Claims, 6 Drawing Sheets

FLUORESCENCE DIAGNOSTIC APPARATUS

BACKGROUND OF THE INVENTION

The invention relates to a fluorescence diagnostic apparatus which conducts spectrometry on fluorescence emitted from a living tissue of a patient and diagnoses whether a tumor site exists or not.

It is known that, when a living tissue is irradiated with light of a wavelength of 420 to 480 nm (excited light), an intrinsic substance (for example, NADH and FMN) of the living tissue is excited to emit fluorescence. Furthermore, it has been revealed that fluorescence emitted from a normal site of a living tissue is different in spectrum from that emitted from a tumor site. Specifically, as shown in FIG. 9, fluorescence emitted from a normal site of a living tissue has a spectrum in which the green region is considerably stronger than the red region, and fluorescence emitted from a tumor site of a living tissue has a spectrum in which the red and green regions are slightly different in intensity from each other. Conventionally, a fluorescence diagnostic apparatus using this phenomenon has been proposed. In the apparatus, fluorescence is guided by a light receiving probe to the outside of a living body, the spectrum of the fluorescence is measured by a spectroscope disposed outside the living body, and a diagnosis on whether a tumor exists in the living body or not is conducted.

FIG. 10 is a diagram showing the configuration of a part of such a fluorescence diagnostic apparatus. Referring to FIG. 10, a light guide 102 of an endoscope 101 irradiates a living tissue O to be diagnosed, with excited light which is introduced from a light source (not shown) that is connected to the basal end of the light guide. The surface of the living tissue O which is irradiated with the light is observed by the operator via an image guide 103 of the endoscope 101. A light receiving probe 100 which is connected to a spectroscope (not shown) disposed outside the living body is guided to the living tissue O which is to be diagnosed, through a forceps channel of the endoscope 101. The light receiving probe 100 conveys fluorescence produced from a site (the living tissue O) which is in front of the probe, to the spectroscope (not shown). The operator adjusts the direction of the tip end portion of the endoscope 101, while observing the living tissue O to be diagnosed via the image guide 103 of the endoscope 101, thereby directing the light receiving probe 100 to each site of the living tissue O. The site to which the light receiving probe 100 is directed is diagnosed whether it is normal or not, based on the spectrum measured by the spectroscope which is not shown.

In the thus configured fluorescence diagnostic apparatus of the prior art, however, movement of the light receiving probe 100 with respect to the endoscope 101 (movement in a direction perpendicular to the center axis of the endoscope 101) cannot be conducted. In order to move the light receiving probe 100, therefore, the tip end of the endoscope must be operated so as to be bent. During the operation of bending the tip end of the endoscope, the range which is to be observed via the image guide 103 is moved. Therefore, the operation of directing the tip end of the light receiving probe 100 to a desired site is very cumbersome and requires the operator to have a high skill. Furthermore, it is difficult to move the tip end of the light receiving probe 100 so as to follow the motion of the diagnostic site during a diagnosis, and hence the tip end of the light receiving probe 100 is frequently positionally misaligned with the diagnostic site. As a result, a diagnosis focused only on a specific diagnostic site is made difficult to do, and the reliability of the diagnosis is lowered.

SUMMARY OF THE INVENTION

In view of the above-discussed problems, it is an object of the invention to provide a fluorescence diagnostic apparatus in which a site to be subjected to spectrometry can be designated in an image of a diagnostic living tissue which is taken via an endoscope, without moving a visual field (an image of the diagnostic living tissue) to be observed via the endoscope, and the designated site can be automatically subjected to spectrometry.

To attain the above-noted object, the present invention provides a fluorescence diagnostic apparatus wherein a light introducing member such as a spectromy-fiber probe is movably arranged to pick up a light from an image of a diagnostic living tissue which is taken via an endoscope. Therefore, the diagnostic site can be moved without moving a visual field (an image of the diagnostic living tissue) which is to be observed via the endoscope.

In a preferable embodiment, the fluorescence diagnostic apparatus comprises: an excited light irradiating mechanism which irradiates a living tissue with excited light; an optical system which transmits light from the living tissue due to the excited light from the excited light irradiating mechanism, and which forms an image of the living tissue; an optical path splitting mechanism which splits an optical path for the light from the living tissue, the light passing through the optical system; an imaging mechanism which takes an image of the living tissue which is formed in one of optical paths split by the optical path splitting mechanism; a light introducing member disposed in an image plane of the living tissue which is formed in another one of the optical paths split by the optical path splitting mechanism, wherein the light introducing member introduces light which constitutes a part of the image of the living tissue; a wavelength selecting optical element which eliminates components of the excited light from the light from the living tissue, in an optical path between the living tissue and the imaging mechanism, and in an optical path between the living tissue and the light introducing member; a spectroscope which conducts spectrometry on the light introduced by the light introducing member; a display device which displays the image of the living tissue which is taken by the imaging mechanism; a pointing device which designates a diagnostic site in the image of the living tissue which is displayed on the display device; and a moving mechanism which moves the light introducing member to a site which is equivalent to the diagnostic site in the image of the living tissue, the diagnostic site being designated by the pointing device.

In the thus configured fluorescence diagnostic apparatus, a living tissue which is irradiated with excited light by the excited light irradiating mechanism emits fluorescence having a spectrum corresponding to the state of the living tissue. The optical system conveys the fluorescence. The optical path splitting mechanism splits an optical path for the light from the living tissue which is transmmitted by the optical system, into plural optical paths. The fluorescence which propagates through each of the split optical paths is converged by the function of the optical system to form an image of the living tissue. The wavelength selecting optical element eliminates frequency components identical with those of the excited light from the light from the living tissue, in front of or in rear of the split by the optical path splitting mechanism. Therefore, all the images of the living tissue respectively formed in the optical paths consist of components of the fluorescence only. The image formed in one of the optical paths is taken by the imaging mechanism, and the image is displayed on the display device. When the diagnostic site in the image of the living tissue which is displayed on the display device is designated by the pointing device, the moving mechanism moves the light guiding member to a site of the living tissue image formed on the other optical path, the site being equivalent to the diagnostic site in the image of the living tissue, the diagnostic site being designated by the pointing device. The light guiding member then guides light which constitutes a portion equivalent to the diagnostic site, to the spectroscope. The spectroscope conducts spectrometry on the introduced light. According to the thus configured fluorescence diagnostic apparatus, a diagnostic site can be designated in the image displayed on the display device, by the pointing device, and the designated site is subjected to spectrometry. Therefore, it is not required to move the visual field which is observed via the image guide of the endoscope, in order to move the fluorescence diagnostic site.

Optical members such as lenses constituting the optical system may be disposed only in front of the optical path splitting mechanism, or alternatively disposed separately both in front and rear of the optical path splitting mechanism. In the latter case, optical members disposed in rear of the optical path splitting mechanism may be disposed respectively in the optical path split by the optical path splitting mechanism. In the latter case, moreover, optical members disposed in front of the optical path splitting mechanism may cooperate with those disposed in rear of the optical path splitting mechanism so as to constitute a relay optical system.

The light guiding member may be an optical fiber bundle or lenses. In the former case, the spectroscope may be fixedly disposed and the tip end of the optical fiber bundle may be moved by the moving mechanism. In the latter case, the spectroscope may be moved integrally with the lenses.

The wavelength selecting optical element may be a filter or a dichroic mirror which blocks only the components of the excited light in the light propagating in the optical paths and allows the other components to pass through the element, or a dichroic mirror which allows only the components of the excited light in the light propagating in the optical paths to pass through the element and reflects the other components. Only one wavelength selecting optical element which is disposed in front of the optical path splitting mechanism may be used, or wavelength selecting optical elements may be disposed in the optical paths in rear of the optical path splitting mechanism, respectively.

The pointing device may be a touch panel which is overlaid on a display screen of the display device, or a mouse, a track ball, or a digitizer which moves a cursor displayed on the display screen of the display device.

The moving mechanism may be a moving table such as an X-Y table.

It is preferable that the light guiding mechanism is an optical fiber or an optical fiber bundle which is connected at a basal end to the spectroscope.

It is preferable that the moving mechanism has a moving table which moves a tip end of the optical fiber bundle in an image plane of the image of the living body.

It is preferable that the moving table is an X-Y table.

It is preferable that the pointing device is a touch panel which is overlaid on a display screen of the display device, or a mouse which designates the diagnostic site by moving a display position of a cursor displayed on a display screen of the display device.

The present disclosure relates to the subject matter contained in Japanese patent application No. 9-112854 (filed on Apr. 30, 1997) which is expressly incorporated herein by reference in its entirety.

DETAILED DESCRIPTION OF A FLUORESCENCE DIAGNOSTIC APPARATUS

Figure 1:
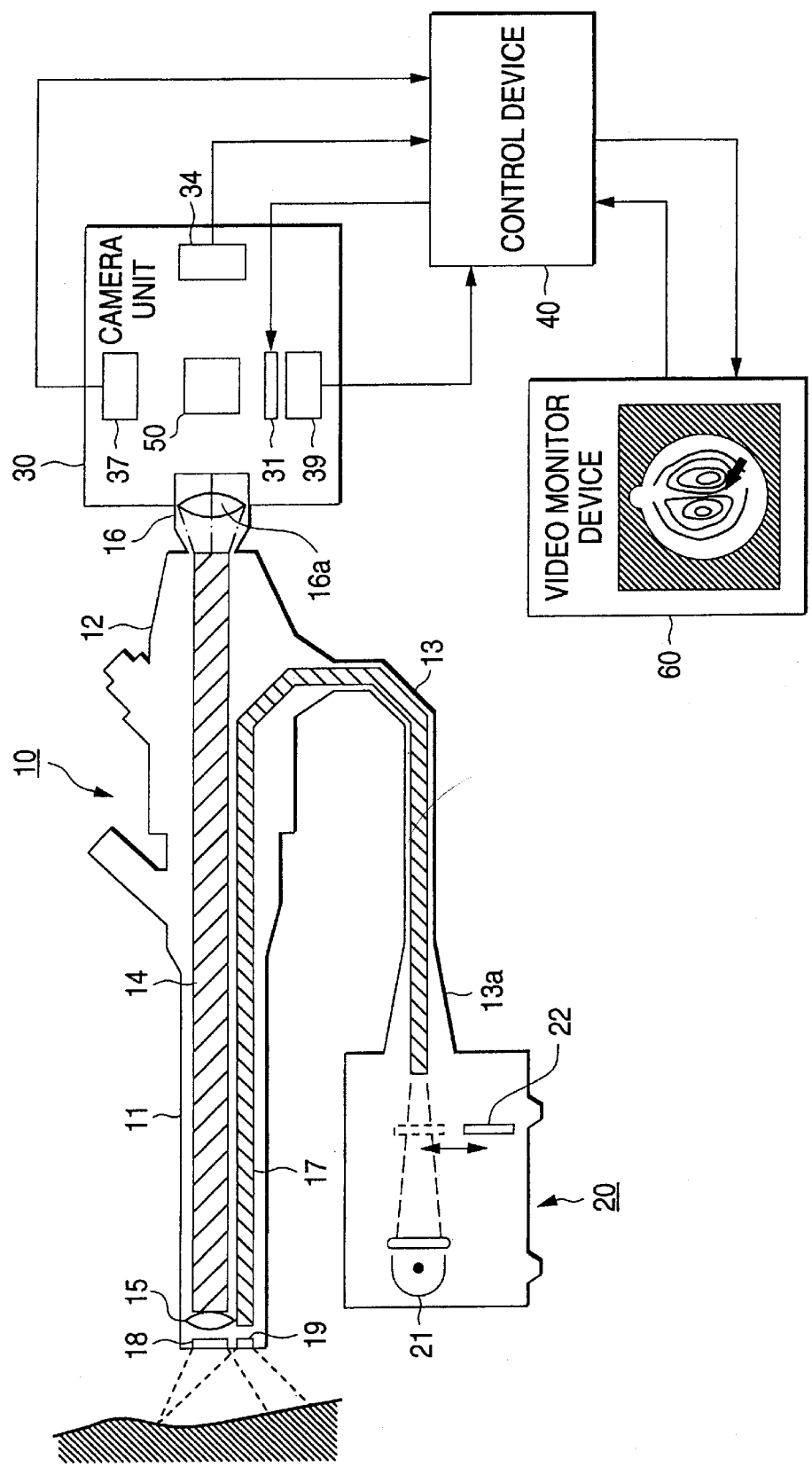
FIG. 1 is a diagram showing the whole configuration of a fluorescence diagnostic apparatus.

Hereinafter, a fluorescence diagnostic apparatus will be described with reference to the accompanying drawings.
Configuration of the fluorescence diagnostic apparatus FIG. 1 is a view showing the internal configuration of a fluorescence diagnostic apparatus. Referring to FIG. 1, the fluorescence diagnostic apparatus is generally configured by an endoscope 10, a light source 20 which supplies light for illuminating an object to the endoscope 10, a camera unit 30 which images an image taken by the endoscope 10, a control device 40 which processes image data produced by the camera unit 30, and a video monitor device 60 which displays the image data processed by the control device 40. Hereinafter, these components will be separately described.
Endoscope The endoscope 10 comprises: an insertion portion 11 which consists of a long flexible tube and which is to be inserted into a body cavity of a patient; an operation portion 12 which is coupled to the basal end of the insertion portion 11 and which is operated by the operator from the outside of the body cavity of the patient; and a long light guide coupling tube 13 which elongates from the outer peripheral face of the operation portion 12. An eyepiece 16 is disposed at an end portion (the end portion which is opposite to the insertion portion 11) of the operation portion 12. The endoscope 10 is detachably connected to the camera unit 30 via the eyepiece 16. A connector 13a is disposed at the tail end of the light guide coupling tube 13. The endoscope 10 is detachably connected to the light source 20 via the connector 13a.

In the endoscope 10, a light guide fiber bundle 17 is passed from the tail end of the connector 13a to the tip end of the insertion portion 11. The end face of the light guide fiber bundle 17 on the side of the connector 13a serves as an incident end face, and that on the side of the insertion portion 11 as an emission end face. When the connector 13a is connected to the light source 20, the incident end face of the light guide fiber bundle 17 is opposed to the interior of the light source 20. By contrast, the emission end face of the light guide fiber bundle 17 is disposed in parallel with an objective optical system 15 provided in the tip end of the insertion portion 11, and an illumination window 19 consisting of a negative lens is disposed in front of the emission end face. Therefore, illumination light introduced from the incident end face of the light guide fiber bundle 17 is transmitted to the emission end face via the light guide fiber bundle 17, and then impinged onto the observation object (the inner wall of the body cavity of the patient) via the illumination window 19.

Furthermore, in the endoscope 10, an image guide fiber bundle 14 is passed from the tip end of the insertion portion 11 to the eyepiece 16. The end face of the image guide fiber bundle 14 on the side of the insertion portion 11 serves as an incident end face, and that on the side of the operation portion 12 as an emission end face. The objective optical system 15 which forms an image of the object in the incident end face of the image guide fiber bundle 14, and an observation window 18 consisting of a plane parallel glass are incorporated in the tip end of the insertion portion 11. On the other hand, an eye lens 16a which is used for observing the image conveyed to the emission end face of the image guide fiber bundle 14 is incorporated in the eyepiece 16. When the camera unit 30 is connected to the eyepiece 16, the eye lens 16a is moved to a position of 0 diopter by an interlocking mechanism which is not shown. According to this configuration, light from the observation object (the inner wall of the body cavity of the patient) which is in front of the tip end of the insertion portion 11 enters the interior of the endoscope through the observation window 18, and is then converged by the objective optical system 15 to form an object image on the incident end face of the image guide fiber bundle 14. The object image is conveyed to the eyepiece 16 by the image guide fiber bundle 14 and then introduced into the camera unit 30 via the eye lens 16a. When lenses of the camera unit 30 are designed and disposed in consideration of the existence of the eye lens 16a, the interlocking mechanism for moving the eye lens 16a may be omitted.

Light source

In the light source 20, a light source lamp 21 using a xenon lamp is disposed at a position opposed to the incident end face of the light guide fiber bundle 17. The illumination light (white light) emitted from the light source lamp 21 is condensed by a reflector disposed in the back of the lamp and then incidents on the incident end face of the light guide fiber bundle 17.

In the illumination optical path between the light source lamp 21 and the incident end face of the light guide fiber bundle 17, an excited-light filter 22 which allows light of a wavelength region of 420 to 480 nm (the excited light) to pass therethrough is disposed so as to be advanced and retracted by a solenoid which is not shown. When a conventional observation is to be conducted, the excited-light filter 22 is retracted to the outside of the illumination optical path so that the whole wavelength region of the illumination light (white light) incidents on the light guide fiber bundle 17. When a fluorescence observation is to be conducted, the excited-light filter 22 is inserted into the illumination optical path so that only the components of the excited light (blue light) of the illumination light (white light) incidents on the light guide fiber bundle 17.

Figure 9:
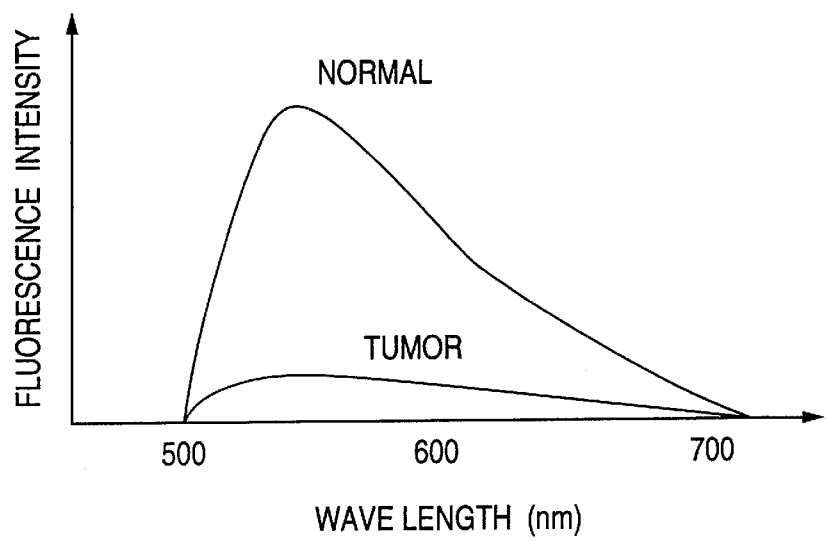
FIG. 9 is a graph showing spectra of fluorescence from a normal portion and that from a tumor portion.
Figure 10:
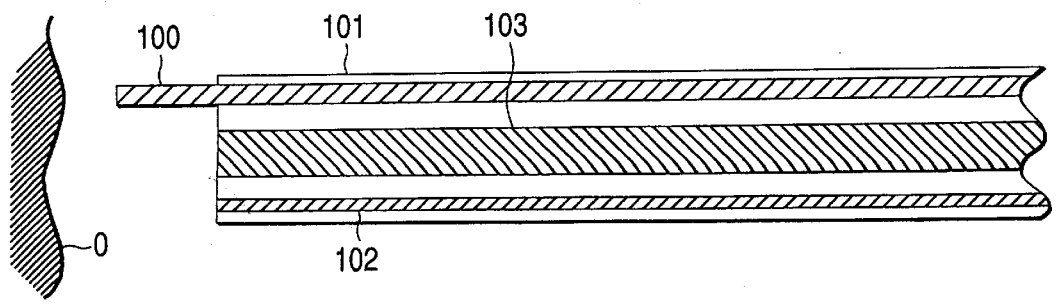
FIG. 10 is a diagram showing the configuration of a part of a fluorescence diagnostic apparatus.

When the excited light incidents on the light guide fiber bundle 17 in this way and the inner wall of the body cavity of the patient is then illuminated with the excited light via the illumination window 19, fluorescence having a spectrum as shown in FIG. 9 is emitted from each site in accordance with the state (normal/tumor) of the living tissue of the inner wall of the body cavity. As a result, an image (a fluorescence observation image of the inner wall of the body cavity) having a fluorescence distribution corresponding to the states of the sites of the living tissue is conveyed to the eyepiece 16 of the endoscope 10.

Camera unit

Figure 2:
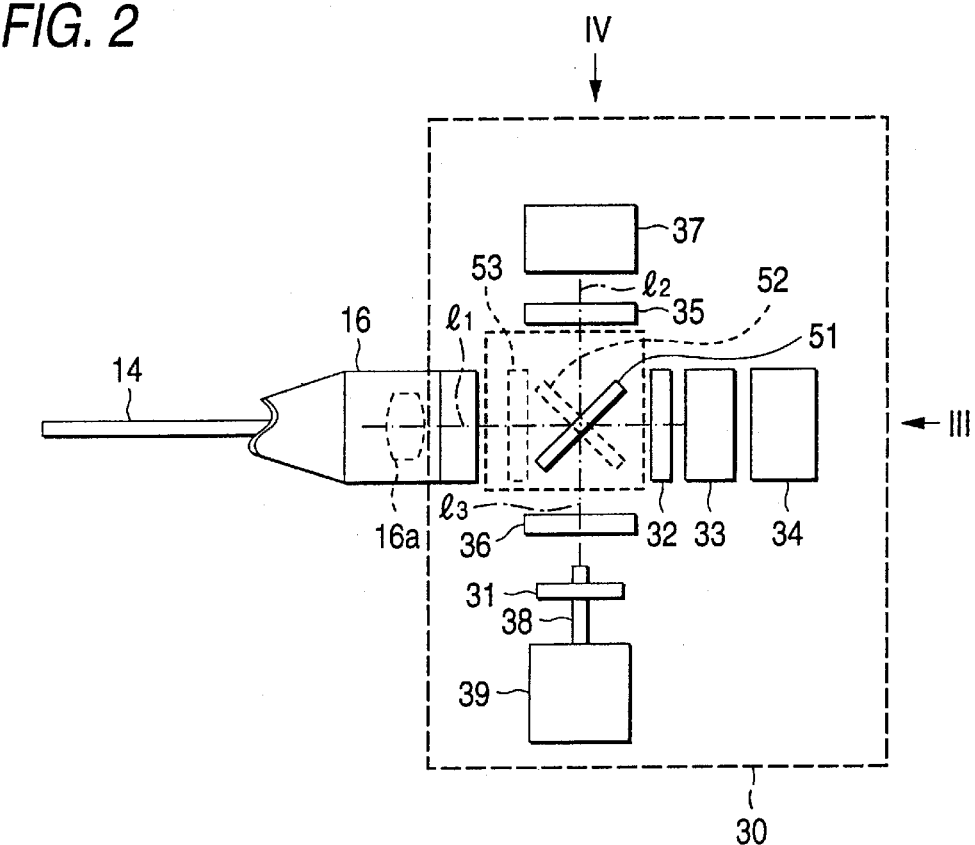
FIG. 2 is a view showing the optical configuration of a camera unit of FIG. 1.
Figure 3:
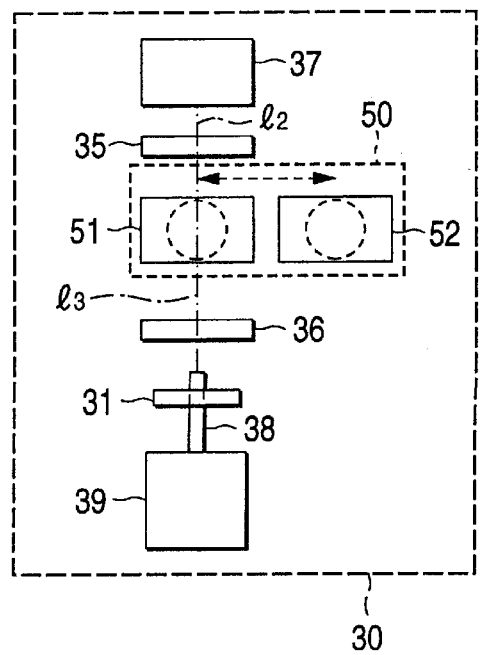
FIG. 3 is a view showing the optical configuration as seen in the direction of the arrow III of FIG. 2.
Figure 4:
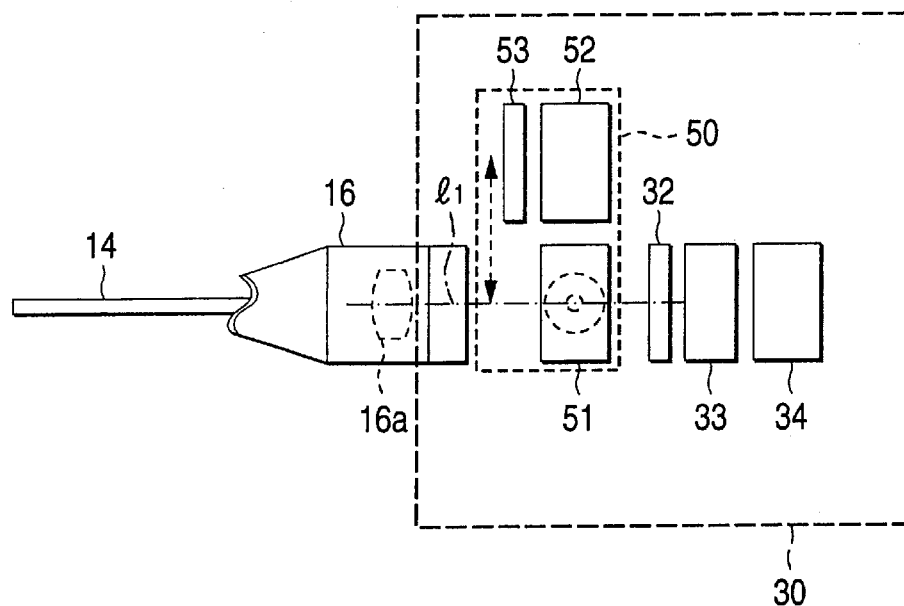
FIG. 4 is a view showing the optical configuration as seen in the direction of the arrow IV of FIG. 2.
Figure 7:
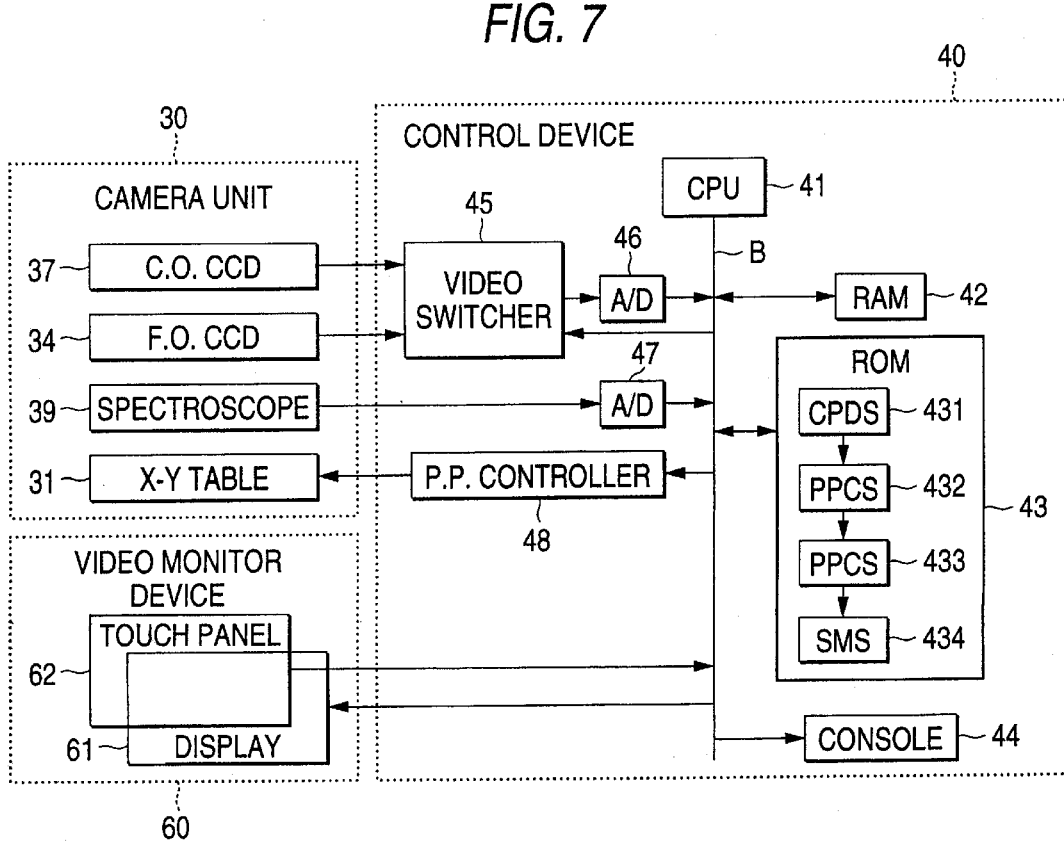
FIG. 7 is a block diagram showing the circuit configuration of a camera unit, a control device, and a video monitor device of FIG. 1.

Next, the internal configuration of the camera unit 30 will be described. FIG. 2 is a view showing the optical configuration of the camera unit 30 as seen in the same direction as that of FIG. 1, FIG. 3 is a view as seen in the direction of the arrow III of FIG. 2, and FIG. 4 is a view as seen in the direction of the arrow IV of FIG. 2. Circuit blocks in the camera unit 30 are shown in FIG. 7.

As shown in these figures, in the camera unit, a mirror box 50, an imaging lens 32, an image intensifier 33, and a fluorescence-observation CCD 34 are arranged in this sequence along the optical axis $l_1$ of the eye lens 16a. In the mirror box 50, two imaging lenses 35 and 36 are disposed with sandwiching the mirror box 50 between the lenses, in lines (optical axes $l_2$ and $l_3$) which are perpendicular to the optical axis of the eye lens 16a. A conventional-observation CCD 37 is disposed in the back of the one imaging lens 35. An X-Y table 31 holding the tip end of a spectrometry-fiber probe 38 (the optical fiber or optical fiber bundle), and a spectroscope 39 which is connected to the basal end of the spectrometry-fiber probe 38 are disposed in the back of the other imaging lens 36. In the apparatus, the spectroscope 39 is disposed in the camera unit 30. Alternatively, the spectroscope may be disposed outside the camera unit 30.

The mirror box 50 is disposed so as to be slidably moved by a manual operation of the operator in the direction perpendicular to the sheet of FIGS. 1 and 2 (the lateral direction in FIG. 3 and the vertical direction in FIG. 4). In the mirror box 50, a total reflection mirror 51 which bends the optical axis $l_1$ of the eye lens 16a toward the conventional-observation CCD 37 so as to coincide with the optical axis $l_2$ of the imaging lens 35, and a partial reflection mirror 52 (the optical path splitting mechanism) which bends the optical axis $l_1$ of the eye lens 16a toward the spectroscope 39 so as to coincide with the optical axis $l_3$ of the imaging lens 36 are juxtaposed in the sliding direction of the mirror box 50. When the mirror box 50 is slidingly moved to the position shown in FIGS. 2 to 4, therefore, the total reflection mirror 51 is inserted into the optical axis $l_1$ of the eye lens 16a so that light emitted through the eye lens 16a is totally reflected toward the imaging lens 35 on the side of the conventional-observation CCD 37. When the mirror box 50 is slidingly moved to the near side in FIG. 2 (to the left side in FIG. 3 and the lower side in FIG. 4), the partial reflection mirror 52 is inserted into the optical axis $l_1$ of the eye lens 16a, with the result that 75 to 95% of light emitted through the eye lens 16a is transmitted toward the imaging lens 32 on the side of the fluorescence-observation CCD 34, and 25 to 5% of the light is reflected toward the imaging lens 36 on the side of the spectroscope 39.

Figure 5:
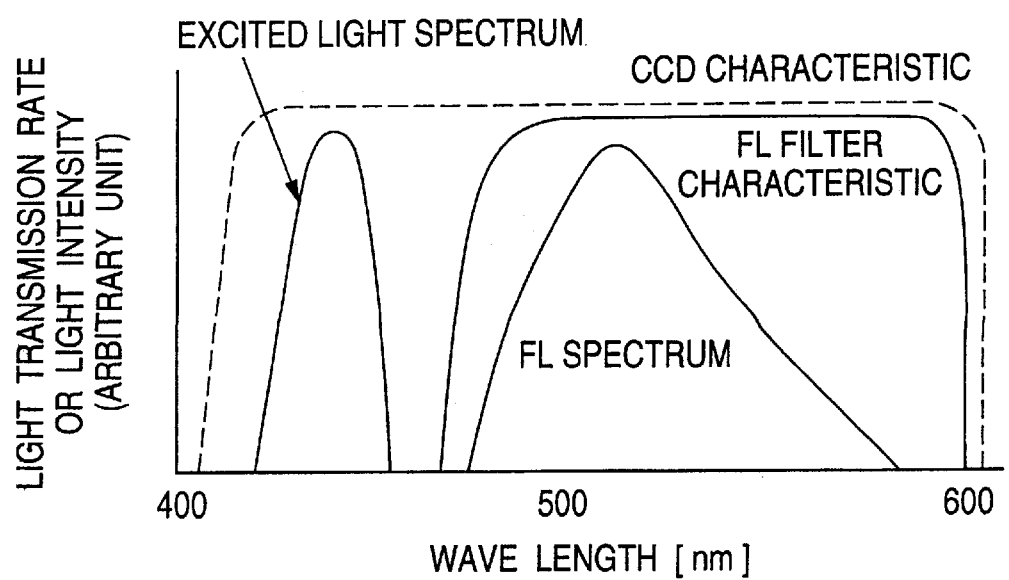
FIG. 5 is a spectral characteristic diagram showing an excited light spectrum, a fluorescence spectrum, and spectral characteristics of an FL filter.

An FL filter 53 (the wavelength selecting optical element) is disposed in front of the partial reflection mirror 52 in the mirror box 50 (on the side of the eye lens 16a) so as to be moved integrally with the partial reflection mirror 52 in accordance with the slide movement of the mirror box 50. As shown in a spectral characteristic diagram of FIG. 5, the FL filter 53 has spectral characteristics in which light of the wavelength region (420 to 480 nm) corresponding to the excited light is cut off, and only light of the wavelength region (480 to 580 nm) corresponding to the fluorescence is allowed to pass through the filter. When the excited-light filter 22 is inserted into the illumination optical path in the light source 20 and the partial reflection mirror 52 and the FL filter 53 are inserted into the optical axis $l_1$ of the eye lens 16a, therefore, only the reflection light component of the excited light in the light (the fluorescence and the reflection light of the excited light) emitted through the eye lens 16a is cut off, and only the fluorescence component incidents on the imaging lens 32 on the side of the fluorescence-observation CCD 34 and the imaging lens 36 on the side of the spectroscope 39.

When the total reflection mirror 51 is inserted into the optical axis $l_1$ of the eye lens 16a, the imaging lens 35 on the side of the conventional-observation CCD 37 cooperates with the eye lens 16a to constitute a relay lens system, so that an image appearing on the emission end face of the image guide fiber bundle 14 is again formed on the imaging plane of the conventional-observation CCD 37.

The conventional-observation CCD 37 is a color CCD which is sensitive to the whole of the visible light region. When the excited-light filter 22 is retracted from the illumination optical path in the light source 20 and the total reflection mirror 51 is inserted into the optical axis $l_1$ of the eye lens 16a, the conventional-observation CCD 37 conducts a color imaging operation on a conventional observation image of the observation object (the inner wall of the body cavity of the patient), and color image data produced by the imaging operation (hereinafter, such data are referred to as "conventional image data") are supplied to the control device 40 (a video switcher 45) (see FIGS. 1 and 7).

When the partial reflection mirror 52 is inserted into the optical axis $l_1$ of the eye lens 16a, the imaging lens 32 on the side of the fluorescence-observation CCD 34 cooperates with the eye lens 16a to constitute a relay lens system, so that an image appearing on the emission end face of the image guide fiber bundle 14 is again formed on the incident face of the image intensifier 33. In other words, the objective optical system 15, the image guide fiber bundle 14, the eye lens 16a, and the imaging lens 32 correspond to the optical system which conveys light from the living body and forms an image of the living body.

The image intensifier 33 is a device which amplifies the brightness of an image (an optical image) formed on the incidence face and then emits the image through the emission face. An imaging lens (not shown) which relays the image emitted through the emission face of the image intensifier 33 to the incident face of the fluorescence-observation CCD 34 is disposed between the emission face of the image intensifier 33 and the incident face of the fluorescence-observation CCD 34.

The fluorescence-observation CCD 34 (the imaging mechanism) is a color CCD which is sensitive to the whole of the visible light region. When the excited-light filter 22 is inserted into the illumination optical path in the light source 20 and the FL filter 53 and the partial reflection mirror 52 are inserted into the optical axis $l_1$ of the eye lens 16a, the fluorescence-observation CCD 34 conducts a color imaging operation on a fluorescence observation image of the observation object (the inner wall of the body cavity of the patient), and color image data produced by the imaging operation (hereinafter, such data are referred to as "fluorescence image data") are supplied to the control device 40 (the video switcher 45) (see FIGS. 1 and 7). Alternatively, the fluorescence-observation CCD 34 may be a monochromatic CCD.

When the partial reflection mirror 52 is inserted into the optical axis $l_1$ of the eye lens 16a, the imaging lens 36 on the side of the spectroscope 39 cooperates with the eye lens 16a to constitute a relay lens system, so that an image appearing on the emission end face of the image guide fiber bundle 14 is again formed as an aerial image. In other words, the objective optical system 15, the image guide fiber bundle 14, the eye lens 16a, and the imaging lens 36 correspond to the optical system which conveys light from a living body and forms an image of the living body. Since the imaging lens 36 on the side of the spectroscope 39 and the imaging lens 32 on the side of the fluorescence-observation CCD 34 have the same focal length and their positions are equivalent to each other, also the magnifications of the imaging lenses 32 and 36 are equal to each other. Therefore, the images of the living body which are respectively formed by the imaging lenses 32 and 36 are strictly identical with each other. In the case where the focal lengths and magnifications of the imaging lenses 32 and 36 are known, however, these values are not particularly required to be equal to each other.

The X-Y table 31 is a table which holds the tip end of the spectrometry-fiber probe 38 parallel with the optical axis $l_3$ and which allows the tip end to be freely moved in a plane perpendicular to the optical axis $l_3$. The incident face of the spectrometry-fiber probe 38 which is held by the X-Y table 31 is positioned in the imaging plane of the fluorescence observation image (the aerial image) which is formed by the imaging lens 36 when the excited-light filter 22 is inserted into the illumination optical path in the light source 20 and the FL filter 53 and the partial reflection mirror 52 are inserted into the optical axis $l_1$ of the eye lens 16a.

Figure 6:
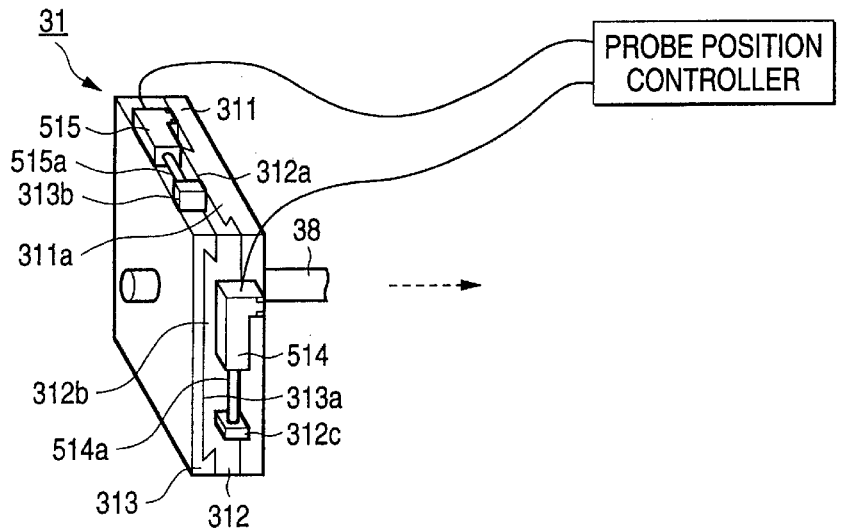
FIG. 6 is a perspective view specifically showing the configuration of an X-Y table of FIG. 2.

FIG. 6 is a perspective view specifically showing the configuration of the X-Y table 31. As shown in FIG. 6, the X-Y table 31 consists of: a stationary table 311 which is fixed to a frame (not shown) in the camera unit 30; an X-table 312 which is slidingly movable in the X-direction (the lateral direction in FIG. 2) with respect to the stationary table 311; and a Y-table 313 which is slidingly movable in the Y-direction (the direction perpendicular to the sheet of FIG. 2) with respect to the X-table 312 and which directly holds the tip end of the spectrometry-fiber probe 38.

The stationary table 311 has a rectangular frame shape as seen from the imaging lens 36. In the frame shape, a rectangular hole (not shown) through which the spectrometry-fiber probe 38 is movably passed is opened at the center. A dovetail 311a which is directed in the X-direction is projectingly formed on the front face (the face contacting with the X-table 312) of the stationary table 311 (excluding the portion of the rectangular hole).

In the same manner as the stationary table 311, the X-table 312 has a rectangular frame shape as seen from the imaging lens 36. A dovetail groove 312a which is engaged with the dovetail 311a of the stationary table 311 is formed on the back face (the face contacting with the stationary table 311) of the X-table 312. A dovetail 312b which is directed in the Y-direction is projectingly formed on the front face (the face contacting with the Y-table 313) of the X-table 312 (excluding the portion of the rectangular hole).

A projection piece 312c is projectingly formed on a side face of the X-table 312 which extends in the X-direction. On the other hand, an actuator 514 opposed to the projection piece 312c is attached to a side face of the stationary table 311 which is flush with the above-mentioned side face. The actuator 514 is controlled by the control device 40 (a probe position controller 48) so that, when a rod 514a is projected to push out the projection piece 312c, the X-table 312 is slidingly moved to the lower portion of FIG. 6, and, when the rod 514a is retracted to pull in the projection piece 312c, the X-table 312 is slidingly moved to the upper portion of FIG. 6.

The Y-table 313 has a rectangular frame shape as seen from the imaging lens 36. The outer edge of the rectangular frame shape has the same dimensions as that of the stationary table 311. The spectrometry-fiber probe 38 is passed through and fixed to the center of the table. A dovetail groove 313a which is engaged with the dovetail 312a of the X-table 312 is formed on the back face (the face contacting with the X-table 312) of the Y-table 313.

A projection piece 313b is projectingly formed on a side face of the Y-table 313 which extends in the Y-direction. On the other hand, an actuator 515 opposed to the projection piece 313b is attached to a side face of the X-table 312 which is flush with the above-mentioned side face. The actuator 515 is controlled by the control device 40 (the probe position controller 48) so that, when a rod 515a is projected to push out the projection piece 313b, the Y-table 313 is slidingly moved to the near side in FIG. 6, and, when the rod 515a is retracted to pull in the projection piece 313b, the Y-table 313 is slidingly moved to the far side in FIG. 6.

According to this configuration, the X-Y table 31 moves the tip end of the spectrometry-fiber probe 38 to an arbitrary position in the imaging plane of the fluorescence observation image (the aerial image), so that light converged at this position can be introduced into the spectrometry-fiber probe 38.

The spectroscope 39 is a device which splits the light introduced by the spectrometry-fiber probe 38 into portions respectively corresponding to frequency regions and which measures the light amounts (namely, conducts spectrometry), thereby measuring the spectrum of the introduced light. The spectral data measured by the spectroscope 39 are supplied to the control device 40 (an A/D converter 47) (see FIGS. 1 and 7).

Video monitor device

FIG. 7 diagrammatically shows the configuration of the video monitor device 60. As shown in FIG. 7, the video monitor device 60 is provided with a display 61 (the display device) on which an image is displayed in accordance with the image data (the conventional image data or the fluorescence image data) supplied from the control device 40. A touch panel 62 (the pointing device) is applied to the surface of the display 61. The touch panel 62 is a device which has many linear transparent electrodes which are arranged into a net-like shape, and a transparent dielectric film sandwiched between the electrodes, and which detects the position of a portion pressed by a finger or a touch pen on the basis of a change of the electrostatic capacity between the electrodes. As shown in FIG. 7, the position information detected by the touch panel 62 is supplied to the control device 40.

Control device

The circuit configuration of the control device 40 is shown in the block diagram of FIG. 7. As shown in FIG. 7, the control device 40 is configured by a CPU 41, a RAM 42, a ROM 43, a console 44, the video switcher 45, an A/D converter 46, the A/D converter 47, and the probe position controller 48 which are connected to each other via a bus B. The video switcher 45 is connected to the A/D converter 46.

The console 44 is an input device such as a keyboard which is mounted on the outer face of a case of the control device 40.

In accordance with switch instructions from the CPU 41, the video switcher 45 selects either of the conventional image data supplied from the conventional-observation CCD 37, and the fluorescence image data supplied from the fluorescence-observation CCD 34, and supplies the selected image data to the A/D converter 46.

The A/D converter 46 analog/digital-converts the image data supplied from the video switcher 45, and supplies the converted data to the CPU 41.

The CPU 41 executes the whole control of the control device 40. Specifically, the CPU 41 outputs switch instructions to the video switcher 45 in accordance with a switch command which is input by the operator through the console 44, and the image data supplied from the A/D converter 46, to the display 61. Furthermore, the CPU 41 executes controls according to programs stored in the ROM 43.

The RAM 42 is a random access memory in which a work area for the CPU 41 is developed.

The ROM 43 is a read only memory which stores programs defining procedures to be executed by the CPU 41. The programs stored in the ROM 43 include a cursor position detecting section 431, a probe position calculating section 432, a probe position controlling section 433, and a spectrometry measuring section 434. The cursor position detecting section 431 detects the position (corresponding to an intra-image position overlapping with the pressed position in the touch panel 62) indicated by the position information supplied from the touch panel 62, in the image data supplied to the CPU 41 by the A/D converter 46. The cursor position detecting section writes a cursor at the detected position in the image data supplied to the display 61. The probe position calculating section 432 calculates a position in the image plane (a position which is equivalent to the display position of the cursor in the image plane due to the imaging lens 36 on the side of the spectroscope 39) which is equivalent to the position detected by the cursor position detecting section 431. The probe position controlling section 433 issues a movement command to the probe position controller 48 so as to move the tip end of the spectrometry-fiber probe 38 to the position in the image face which is calculated by the probe position calculating section 432. The spectrometry measuring section 434 analyzes the spectrum supplied to the CPU 41 by the A/D converter 47, and displays the analysis result (which portion of the inner wall of the body cavity displayed on the display 61 is affected with a tumor) on the display 61.

The A/D converter 47 analog/digital-converts the spectrum supplied from the spectroscope 39 and supplies the converted data to the CPU 41.

In accordance with the movement command received from the CPU 41, the probe position controller 48 supplies driving currents for moving the tip end of the spectrometry-fiber probe 38 to the position included in the movement command, to the actuators 514 and 515 of the X-Y table 31.

Contents of controls

Figure 8:
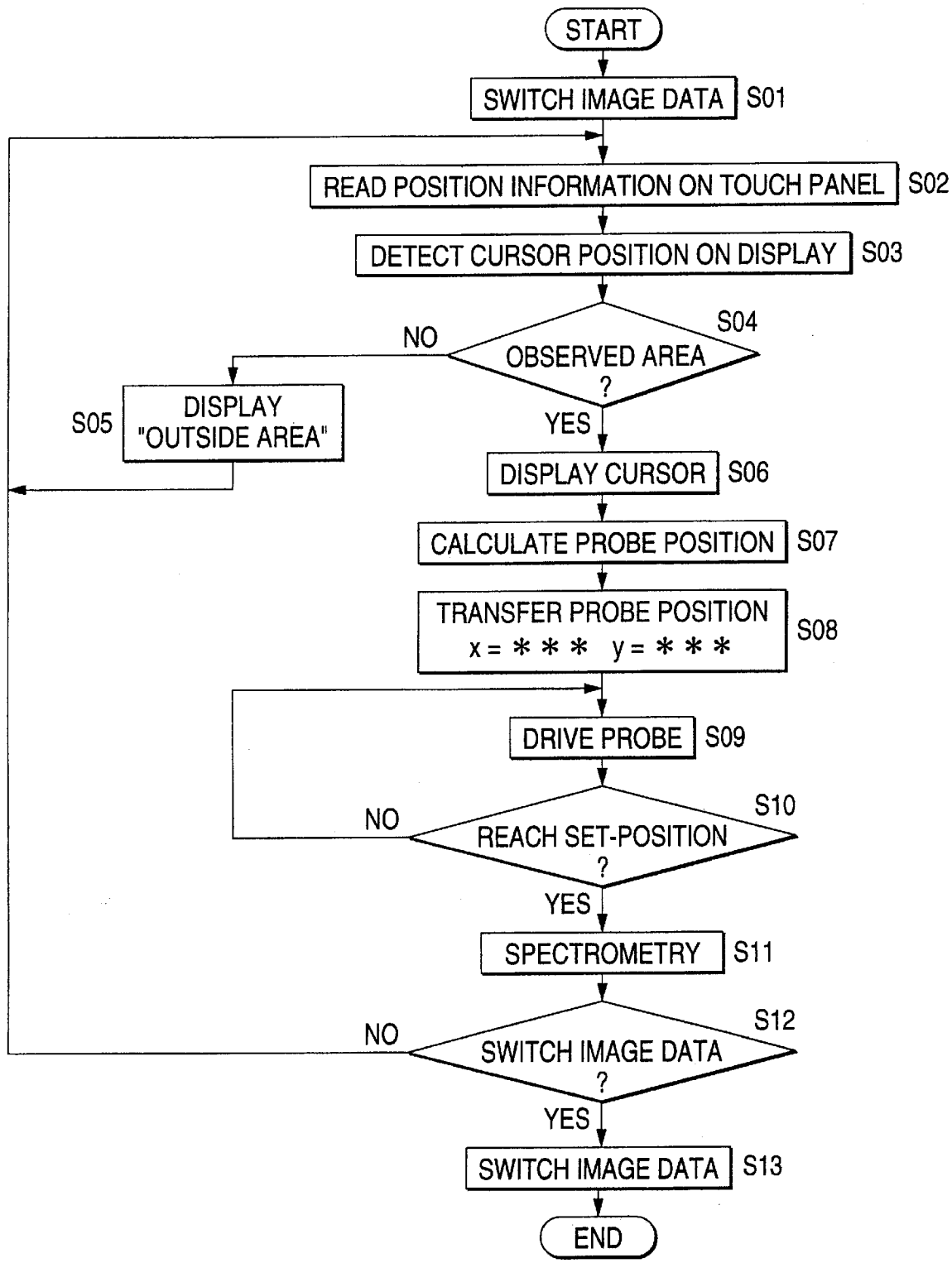
FIG. 8 is a flowchart showing control processing of programs which are stored in a ROM 43 of FIG. 7 and executed by a CPU.

Next, the contents of controls of the CPU 41 according to the programs stored in the ROM 43 will be described with reference to a flowchart of FIG. 8.

The flowchart is started by inputting the switch command to switch over the image to be displayed on the display 61 to the fluorescence image data, through the console 44. In S01 which is first conducted after the start, the CPU 41 gives switch instructions for selecting the fluorescence image data from the fluorescence-observation CCD 34, to the video switcher 45.

In next S02, the CPU 41 fetches the position information output from the touch panel 62.

In next S03, the CPU 41 detects the position of the cursor (the pressed position in the touch panel 62) which is to be displayed on the display 61, on the basis of the position information fetched in S02.

In next S04, the CPU 41 checks whether the cursor position detected in S03 is in a display position for image data (inspection area) of the display 61 or not. If the cursor position is outside the inspection area, the CPU 41 supplies in S05 data for displaying "OUTSIDE AREA" to the display 61, and then returns the process to S02.

By contrast, if the cursor position is in the inspection area, the CPU 41 writes in S06 the image of the cursor at the cursor position which is in the image data supplied from the A/D converter 46 and which is detected in S03, and supplies the resulting image data to the display 61.

In next S07, the CPU 41 calculates the position in the image face of the tip end of the spectrometry-fiber probe 38. The position is equivalent to the cursor position detected in S03.

In next S08, the CPU 41 notifies the probe position controller 48 of the position in the image face (the X-direction position indicative of the position in the X-direction, and the Y-direction position indicative of the position in the Y-direction) which is calculated in S07.

In next S09, the CPU 41 gives to the probe position controller 48 the movement command to move the tip end of the spectrometry-fiber probe 38 to the position in the image face which is notified in S08.

In next S10, the CPU 41 checks whether the movement of the spectrometry-fiber probe 38 corresponding to the movement command in S08 is completed or not. If the movement is not completed, the process is returned to S09.

By contrast, if the movement is completed, the CPU 41 executes in S11 spectrometry on the basis of the spectrum which is supplied from the spectroscope 39 via the A/D converter 47, and displays measurement results on the display 61.

In next S12, the CPU 41 checks whether a switch command to switch over the image to be displayed on the display 61 to the conventional image data is input through the console 44 or not. If the-switch command is not input, the CPU 41 returns the process to S02.

By contrast, if the switch command is input, the CPU 41 gives in S13 switch instructions for selecting the conventional image data from the conventional-observation CCD 37, to the video switcher 45, and then ends the control according to the flowchart.

Function

The procedure of a fluorescence diagnosis of the inner wall of a body cavity which uses the thus configured fluorescence diagnostic apparatus will be described. First, the operator causes the excited-light filter 22 to be retracted from the illumination optical path in the light source 20, and the mirror box 50 of the camera unit 30 to be slidingly moved, so that the total reflection mirror 51 is inserted into the optical axis $l_1$. Furthermore, the operator inputs a switch command into the control device 40 through the console 44, thereby supplying the image data from the conventional-observation CCD 37 to the display 61. As a result, a color image of a body existing in front of the tip end of the insertion portion 11 is displayed on the display 61. While observing the color image on the display 61, the operator inserts the insertion portion 11 into a body cavity of the patient, so that the insertion portion reaches a diagnostic site.

When a color image of the diagnostic site is displayed on the display 61, the operator causes the excited-light filter 22 to be inserted into the illumination optical path in the light source 20, and the mirror box 50 of the camera unit 30 to be slidingly moved, so that the partial reflection mirror 52 and the FL filter 53 are inserted into the optical axis $l_1$. Furthermore, the operator inputs a switch command into the control device 40 through the console 44, thereby supplying the image data from the fluorescence-observation CCD 34 to the display 61. As a result, a fluorescence image of the diagnostic site is displayed on the display 61.

The operator presses a site which is in the fluorescence image displayed on the display 61 and which is to be subjected to spectrometry, through the touch panel 62 with a touch pen, a finger, or the like. Then, the CPU 41 of the control device 40 fetches position information indicative of the pressed site (S02). The CPU 41 detects the site in the image data which corresponds to (overlaps with) the pressed site (S03), and the cursor is displayed at the position in the image.

At the same time, the CPU 41 calculates the position in the image face which is equivalent to the position where the cursor is displayed and which is produced by the imaging lens 36 (S07), and gives to the X-Y table 31 the movement command together with the position data (S08 and S09). The X-Y table 31 which receives the movement command supplies a driving current to the actuator 515 so that the tip end of the spectrometry-fiber probe 38 is moved to the position in the X-direction, and another driving current to the actuator 514 so that the tip end of the spectrometry-fiber probe 38 is moved to the position in the Y-direction. In this way, the tip end of the spectrometry-fiber probe 38 is moved to the position in the image face which is equivalent to the intra-image position where the cursor is displayed. Thereafter, light is introduced from the tip end of the spectrometry-fiber probe 38 and spectrometry is conducted in the spectroscope 39 (S11).

As described above, according to the fluorescence diagnostic apparatus, the operator can designate the diagnostic site by directly pressing the image on the display 61. When the diagnostic site is designated in this way, the tip end of the spectrometry-fiber probe 38 is moved to the position in the image face which is equivalent to the designated diagnostic site, and spectrometry is then conducted on the site. Therefore, it is not required to bend the tip end of the endoscope in order to move the diagnostic site, and only the diagnostic site can be moved in a fixed visual field.

The apparatus may be modified so that the touch panel 62 is eliminated from the video monitor device 60, and, in place of the touch panel, a mouse serving as the pointing device is connected to the CPU 41. In this case, the CPU 41 may move the cursor on the display 61 in accordance with the movement information supplied from the mouse, detect the position where the cursor is displayed, at the timing when a click signal is input from the mouse, and calculate the corresponding probe position.

What is claimed is:

1. A fluorescence diagnostic apparatus comprising:
    an excitation light irradiating mechanism which irradiates a living tissue with excitation light;
    an optical system which transmits light from the living tissue due to the excitation light from said excitation light irradiating mechanism, and which forms an image of the living tissue;
    an optical path splitting mechanism which splits an optical path for the light from the living tissue into first and second optical paths, the light passing through said optical system;
    an imaging mechanism which takes an image of the living tissue that is formed in said first optical path split by said optical path splitting mechanism;
    a light introducing member disposed in an image plane of the living tissue which is formed along said second optical path split by said optical path splitting means, the light introducing member including a movable tip end that receives only a portion of light corresponding to the image of the living tissue;

a wavelength selecting optical element which eliminates components of the excited light from the living tissue, in said first optical path between the living tissue and said imaging mechanism, and in said second optical path between the living tissue and said light introducing member;

a spectroscope which conducts spectrometry on the light received by said movable tip end of said light introducing member;

a display device which displays the image of the living tissue which is taken by said imaging mechanism from said first optical path;

a pointing device which designates a diagnostic site in the image of the living tissue which is displayed on said display device; and a moving mechanism which moves said movable tip end of said light introducing member to a site along said second optical path which is equivalent to the diagnostic site in the image of the living tissue, the diagnostic site being designated by said pointing device.

2. A fluorescence diagnostic apparatus according to claim 1, wherein said light introducing member is an optical fiber or an optical fiber bundle which is connected at a basal end to said spectroscope.

3. A fluorescence diagnostic apparatus according to claim 2, wherein said moving mechanism has a moving table which moves a tip end of said optical fiber bundle in an image plane of the image of the living body.

4. A fluorescence diagnostic apparatus according to claim 3, wherein said moving table is an X-Y table.

5. A fluorescence diagnostic apparatus according to claim 1, wherein said pointing device is a touch panel which is overlaid on a display screen of said display device.

6. A fluorescence diagnostic apparatus according to claim 1, wherein said pointing device is a mouse which designates the diagnostic site by moving a display position of a cursor displayed on a display screen of said display device.

7. A fluorescence diagnostic apparatus for use in an environment including an endoscope having a light guide with a distal end and a proximal end, said fluorescence diagnostic apparatus comprising:

an image forming optical system forming an image of diagnostic living tissue at the proximal end;

a spectrometry fiber probe movably arranged to move with reference to the image of diagnostic living tissue formed at the proximal end of the light guide of the endoscope, said spectrometry fiber probe picking up light from a diagnostic site that is only a portion of the image of diagnostic living tissue, said spectrometry fiber probe substantially excluding light from the remaining portion of the image of diagnostic living tissue that is not within the diagnostic site.

8. The fluorescence diagnostic apparatus according to claim 7, further comprising:

a display device that receives the image of diagnostic living tissue and displays the image of diagnostic living tissue;

a pointing device that receives a designation from an operator indicating the diagnostic site forming only a portion of the image of diagnostic living tissue; and a controller that moves said spectrometry fiber probe substantially perpendicularly to the image of diagnostic living tissue formed at the proximal end of the light guide to pick up light from only the diagnostic site, substantially excluding light from the remaining portion of the image of diagnostic living tissue that is not within the diagnostic site.

* * * * *